United States Patent [19]

Pak et al.

[11] Patent Number: 5,053,493

[45] Date of Patent: Oct. 1, 1991

[54] METHOD FOR LABELING ANTIBODIES WITH A METAL ION

[75] Inventors: Koon Y. Pak, Norristown; Richard T. Dean, Downingtown; Jeffrey A. Mattis, West Chester, all of Pa.

[73] Assignee: Centocor Cardiovascular Imaging Partners, L.P., Malvern, Pa.

[21] Appl. No.: 34,003

[22] Filed: Apr. 2, 1987

[51] Int. Cl.$^5$ .................. C07K 3/08; G01N 33/53; A04N 55/02

[52] U.S. Cl. .................. 530/402; 530/387; 530/388; 530/389; 530/390; 436/547; 436/804; 514/492

[58] Field of Search ............ 530/389, 390, 402, 387, 530/388; 436/547, 548; 424/DIG. 6, 1.1, 9; 534/10, 14; 514/492

[56] References Cited

U.S. PATENT DOCUMENTS

| | | | |
|---|---|---|---|
| 4,027,005 | 5/1977 | Adler et al. | 424/1.1 |
| 4,113,850 | 9/1978 | Benes | 424/1.1 |
| 4,305,922 | 12/1981 | Rhodes | 424/1.1 |
| 4,421,735 | 12/1983 | Haber et al. | 424/1.1 |
| 4,472,371 | 9/1984 | Burchiel et al. | 424/1.1 |
| 4,472,509 | 9/1984 | Gansow et al. | 436/548 |
| 4,478,815 | 10/1984 | Burchiel et al. | 424/1.1 |
| 4,638,051 | 1/1987 | Burns et al. | 534/14 |
| 4,668,503 | 5/1987 | Hnatowich | 424/1.1 |

FOREIGN PATENT DOCUMENTS

| | | |
|---|---|---|
| 0173629 | 3/1969 | European Pat. Off. |
| 0005638 | 11/1979 | European Pat. Off. |
| 0083129 | 7/1983 | European Pat. Off. |
| 0178125 | 4/1986 | European Pat. Off. |
| 0188256 | 7/1986 | European Pat. Off. |
| 0196669 | 10/1986 | European Pat. Off. |
| 0237150 | 9/1987 | European Pat. Off. |
| WO87/00004 | 7/1987 | PCT Int'l Appl. |
| 2109407 | 12/1985 | United Kingdom |

OTHER PUBLICATIONS

Khaw et al., *The Journal of Nuclear Medicine*, 23 (11): 1011-1019.

Ballou et al., *Science*, 206: 844-846 (Nov. 1979).

Eckelman et al., *Nuclear Medicinal Biology*, 13 (4): 335-343 (1986).

Paik et al., *International Journal of Nuclear Medicinal Biology*, 12(1): 3-8 (1985).

Richards and Steigman, *Radiopharmaceuticals*, Chapter 3, pp. 26-30, Subramanian, Rhodes, Cooper and Sodd, Eds., New York, Society of Nuclear Medicine (1975).

*Primary Examiner*—Esther L. Kepplinger
*Assistant Examiner*—Janelle Graeter
*Attorney, Agent, or Firm*—Hamilton, Brook, Smith & Reynolds

[57] ABSTRACT

A simple, rapid and efficient method for labelling sulfhydryl-containing antibodies or antibody fragments with Tc-99m, Rh-186, Rh-188, Rh-189 or Rh-191 is disclosed. Labeled antibodies produced by the method are useful for radio-immunodiagnostic and/or radiotherapeutic purposes.

28 Claims, 1 Drawing Sheet

METHOD FOR LABELING ANTIBODIES WITH A METAL ION

BACKGROUND OF THE INVENTION

Proteins have been labeled with various radiometals and other radioisotopic elements for use in immunodiagnostic and immunotherapeutic procedures. Some radiometals have superior properties for use in these techniques. Technetium-99m is an ideal radionuclide for scintigraphic imaging because of its nuclear properties. It has a single photon energy of 140 keV, a half-life of about 6 hours, and it is readily available from a $^{99}$Mo-$^{99m}$Tc generator. Rhenium radioisotopes are beta-emitters which can kill target cells and thus are useful in therapy. Rhenium-186 and -188 also have gamma emission which, as an added feature, allows it to be imaged by scintigraphic techniques.

Two general approaches have been taken to label proteins such as antibodies with radiometals. The first is the direct labeling method by which the radiometal is bound to the protein molecule itself. The second is the indirect labeling method in which a chelating agent is coupled to the protein and the radiometal is attached to the protein via the chelating agent.

Rhodes discloses a method of direct labeling of protein with technetium-99m which involves ligand solid phase exchange. See U.S. Pat. No. 4,305,922. According to the method of Rhodes, pertechnetate is reduced to technetium IV and then applied onto a Sephadex$^R$ column. The reduced technetium-99m binds to the Sephadex$^R$ material. A solution of the protein to be labeled is poured onto the top of the Sephadex column where it is allowed to remain so that ligand exchange occurs. As a result, the technetium-99m is transferred preferentially from the Sephadex material to the protein. The protein may be pretreated with a stannous chloride (a procedure called "pretinning") to enhance transfer of the radiometal to the protein. See U.S. Pat. No. 4,424,200.

Various attempts have been made to label proteins with radiometals by the indirect approach. In one such approach, a chelating agent such a diethylenetriaminepentaacetic acid (DTPA) is conjugated onto the protein and then the metal ion is labeled onto the chelating agent attached to the protein molecule. For example, Khaw et al., *Science* 209: 295–297 (1980) discloses antibodies to cardiac myosin labeled with indium-111 via DTPA and use of the labeled antibodies to image for myocardial infarction. See also, Krejcarek et al., *Biochem. Biophys. Res. Commun.* 77: 581–585 (1977); Childs, R. L. and Hnatowich, D. J., *J. Nucl. Med.* 26: 293 (1985). In a more recent approach, Fritzberg et al. describe the use particular diaminodithiol and diamidodithiol groups, as a chelating agents. Fritzberg et al, *J. Nucl. Med.* 27:957 (1986); European Patent Application 86100360.6.

Various degrees of success have been achieved with both the direct and indirect methods of labeling proteins with radiometals. However, the labeled product is often unstable in vivo. Further, techniques for purifying the labeled product before use are often required. A need exists for improved methods for stably labeling proteins for radioimmunodiagnostic and radioimmunotherapeutic procedures.

SUMMARY OF THE INVENTION

This invention pertains to a simple, rapid and efficient method of labeling sulfhydryl-containing antibodies or antibody fragments with the radiometals technetium-99m rhenium-186, rhenium-188, rhenium-189 and rhenium-191. In general, the method comprises:

a. forming an aqueous mixture of
   (i) the radiometal in an oxidized form; and
   (ii) a reducing agent and a water-soluble ligand which is capable of forming a stable complex with the radiometal in its reduced state and quantitatively exchanging the radiometal with a sulfhydryl-containing antibody; and b. contacting the mixture with a sulfhydryl-containing antibody or antibody fragment to produce a radiometal-labeled antibody or antibody fragment.

Technetium-99m labeled antibodies or antibody fragment are useful for radioimmunodiagnostic purposes such as immunoscintigraphy. The rhenium labeled antibodies or antibody fragments can be used for therapy.

The preferred ligand is a polyhydroxydicarboxylic acid or salt thereof having a molecular weight of less than about 10,000 daltons. An especially preferred ligand is saccharic acid. Saccharic acid quickly and stably complexes with technetium-99m in its reduced state and without the formation of significant technetium colloids. When contacted with a sulfhydryl-containing antibody, Technetium-99mm is preferentially transferred to the antibody to form a stable labeled antibody.

The preferred reducing agents for use in the method are stannous reducing agents such as stannous chloride. These reagents effectively reduce technetium and are pharmacologically acceptable.

The method of this invention can be used to label whole antibodies (e.g., IgG) or antibody fragments (e.g., Fab'). Whole antibodies can be reduced with the reducing agent dithiothreitol (DTT) for example, to produce sulfhydryl containing antibodies. Fab' fragments are especially suited for labeling by the procedure. Under nonoxidizing conditions, these fragments contain free sulfhydryl groups (as they are produced by reduction of disulfide bridges present in F(ab)'$_2$ fragments. For most radioimmunodiagnostic techniques, antibody fragments such as Fab' fragments are preferred and thus, the labeling procedure of this invention is particularly suited for preparing radiopharmaceuticals for these techniques.

The method of radiolabeling antibody or antibody fragments with the designated radiometals can be performed as a simple two-vial procedure. For this purpose, kits can be provided with the reagents in a form ready for use on site by the clinician. For example, such a kit can include a first vial containing a reducing agent (e.g. stannous ions) and the water soluble ligand (e.g. saccharic acid or a salt thereof) and a second vial containing a Fab' fragment suited for the particular diagnostic or therapeutic procedure. The reactions are preferably carried out in an aqueous medium although the reagents may be supplied in lyophilized, frozen or aqueous form. For the preparation of technetium-99m labeled fragments, technetium-99m (generally in the form of pertechnetate) is added to the first vial and then the contents of the first and second vial are mixed and incubated for a time sufficient to effect a quantitative transfer of the technetium-99m to the Fab' fragment. The composition can then be injected into the patient without purification. For radiolabeling with rhenium, rhenium isotopes (in the form of a perrhenate) are used in place of the technetium. The rhenium labeled Fab' fragment is also suitable for injection without purification.

The technetium-99m-labeled antibodies and antibody fragments prepared by the method of this invention can be used for diagnostic purposes such as immunoscintigraphy of tumor, myocardial infarction, thromboses or bacterial abscess. Rhenium-labeled antibodies can be used to selectively deliver a rhenium radioisotope in vivo for therapy.

The method of this invention has several important advantages. As mentioned, the ligands employed are capable of complexing technetium-99m quantitatively in stable form as a complex without the formation of a significant amount of technetium colloid. Upon contact with a sulfhydryl containing antibody under appropriate conditions, the complexed technetium-99m is transferred substantially quantitatively to sulfhydryl-containing antibodies so that radiodiagnostic composition can be prepared with very high specific activity. The antibody or antibody fragments labeled by the method retain their original immunoreactivity and consequently their target specificity. The radiolabeled antibody is stable in solution and in serum. When Fab' fragments labeled by the method are administered in vivo very little label accumulates in the liver which indicates that the labeled antibody is stable in vivo. In addition, the labeling method can be performed rapidly (it can be completed in less than one hour) and the method can be performed at room temperature and at pH 5-9. The labeled product does not require purification before use.

DETAILED DESCRIPTION OF THE INVENTION

Figure 1:
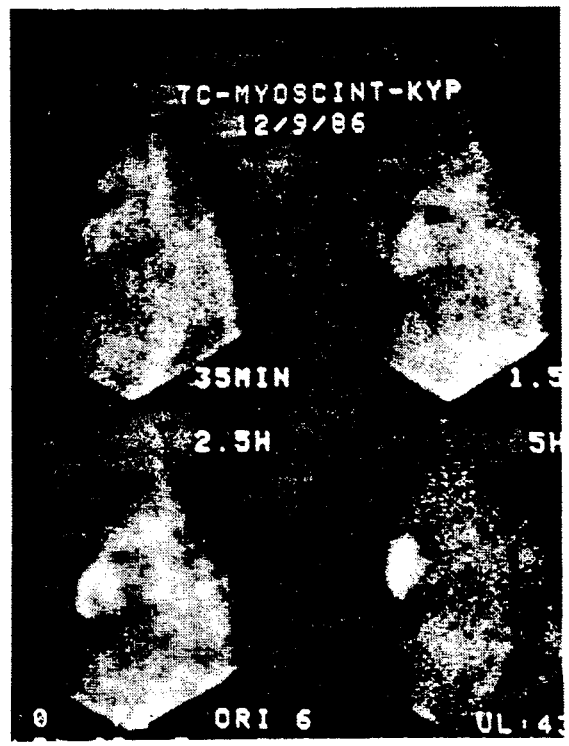
FIG. 1 shows gamma scintigrams of a dog at various times after injection of technetium-99m labeled myosibspecific Fab' fragment.

In one embodiment, the method of this invention is performed by reacting Technetium-99m (in an oxidized state) with a water-soluble ligand in the presence of a reducing agent to form a stable complex between technetium-99m in a reduced state (e.g., IV or V valence state) and the ligand and then reacting the complex with an antibody or antibody fragment which contains one or more sulfhydryl groups. In the preferred embodiment for labeling a sulfhydryl-containing antibody with technetium-99m, aqueous sodium 99m-pertechnetate is mixed with a aqueous solution of a stannous reducing agent and saccharic acid (or a salt thereof) to form a $^{99m}$Tc-saccharate complex. The complex is then contacted with an Fab' fragment and incubated for a period of time and under conditions which allow an exchange of technetium-99m from the complex to the Fab' fragment to form a technetium-labeled Fab' fragment. The entire procedure can be conducted in less than one hour at room temperature and at a pH of about 5-9. Under these conditions an essentially complete transfer of technetium-99m (from the 99m-Tc-saccharate complex to the antibody protein) can be attained without significant loss of antibody immunoreactivity.

The various reagents used in the method and the parameters of the method are discussed in detail below.

The Ligands

In general, the ligands useful in the method of this invention are water-soluble (or can be made water soluble) chelators which are capable of complexing technetium-99m or any of the rhenium radioisotopes in their reduced state to form a stable metal ion/ligand complex. The complex is capable of exchanging the technetium-99 with a sulfhydryl containing antibody or antibody fragment.

Some of the ligands which can be used in the labeling method of this invention are represented by compounds (including physiologically acceptable salts thereof) having the general formula:

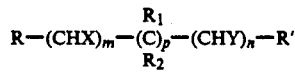

where X and Y are OH or $NH_2$;
R and R' independently H, COOH, or $CH_2OH$ or R and R' taken together can form a ring or bi-or multidentate ligand;
m and n are 0-10, such that m+n is at least 2;
$R_1$ and $R_2$ are independently H, lower alkyl, substituted lower alkyl, aryl and lower alkylaryl; and
p is 0 or 1 provided that, when p is 1, m and n independently are at least 1.

Some of the preferred water soluble ligands for use in the method are represented by the formula:

wherein R and R' are COOH or $CH_2OH$, and $n = 2-10$
Among the ligands represented by this formula, polyhydroxydicarboxylic acids having a molecular weight of less than about 10,000 daltons are most preferred. Some specific examples of these types of ligands are saccharic acid, glucoheptonic acid, tartaric acid, galactaric acid, arabonic acid, and salts thereof.

The particularly preferred ligand for use in this method is saccharic acid. As mentioned, saccharic acid complexes with technetium-99m quickly to form a stable technetium-99m-saccharate complex. Upon contact with a sulfhydryl-containing antibody or antibody fragment, substantially quantitative transfer of technetium-99m from the complex to the protein is achieved rapidly and under mild conditions. As described below, it is believed that the technetium-99m is preferentially transfered to favored binding sites on the protein molecules. This preferential transfer results in a labeled antibody or fragment which is immunoreactive and exceptionally stable in vivo.

Reducing Agents

Reducing agents for use in the method are physiologically acceptable for reducing technetium-99m from its oxidized state to the IV or IV oxidization state or for reducing rhenium from its oxidized state. Examples of reducing agents which can be used in the method are stannous chloride, stannous fluoride, stannous tartarate, and sodium dithionite; the preferred agents are stannous reducing agents especially stannous chloride.

Radioisotopes of technetium and rhenium

The source of Technetium-99m should preferably be water soluble. Preferred sources are alkali and alkaline earth metal pertechnetate ($TcO_4^-$). The technetium- 99m is most preferably obtained in the form of fresh sodium pertechnetate from a sterile technetium-99m generator (e.g., from a conventional 99Mo/99mTc generator). Any other source of physiologically acceptable technetium-99m, however, may be used.

Rhenium radioisotopes (the isotopes 186, 188, 189 and 191) in the form of perrhenate salts can be produced by suitable reactor technology or made by a suitable generator. The perrhenate salts are stable, soluble salts and behave similarly to pertechnetate. Perrhenate requires a slightly greater reduction potential to reduce, and tends to return to perrhenate in the presence of oxygen more readily than pertechnetate. For this reason, different conditions may be required to reduce and stabilize rhenium in its reduced state. These can be ascertained empirically by a person of ordinary skill in the art.

Sulfhydryl-containing antibodies or antibody fragments

The sulfhydryl containing whole antibodies or lower molecular weight antibody fragments can be labeled by the method of this invention. It is believed that sulfhydryl groups constitute at least a part of favored binding sites which exist on molecules and that by the method of this invention, the radiometals are preferentially exchanged from the radiometal-ligand complex to these favored sites on the molecules. The preferential labeling of these sites on the antibodies molecules results in labeled antibodies of exceptional stability.

Whole antibodies (e.g. IgG) can be provided with sulfhydryl groups by reducing the antibodies with a reducing agent such as dithiothreitol DTT. Treatment with DTT exposes the sulfhydryl groups by reducing disulfide bridges.

For most immunodiagnostic procedures, antibody fragments are preferred reagents. Antibody fragments have a number of advantages over whole antibodies for imaging procedures including, in general, more rapid distribution and accumulation at target site and less immunogenicity. Fab' fragments are monovalent antibody binding which contain free sulfhydryl groups (when maintained under nonoxidizing conditions). These fragments can be labelled efficiently by the method of this invention.

Fab' fragments can be prepared from whole antibodies as follows: An antibody molecule is first treated with an endopeptidase such as pepsin to remove the Fc portion of the antibody molecule. The resultant F(ab)'$_2$ fragment is treated with a reducing agent such as DTT or cysteine to break disulfide bonds present on the F(ab)'$_2$ fragment resulting in exposed the sulfhydryl groups present on the molecules and thereby producing two Fab' molecules for each antibody molecule.

Reaction Conditions

The amount of reducing agent is the amount necessary to reduce the technetium to provide for the binding to the ligand in a reduced state. In a preferred mode, stannous chloride (SnCl$_2$) is the reducing agent and can range from 1–1,000 ug/ml preferably about 30–500 ug/ml. The amount of saccharic acid (as potassium saccharate) can range from about 0.5 mg/ml up to the amount maximally soluble in the medium. Preferred amounts of saccharic acid range from 30–15 ug/ml. The amount of antibody (or fragment) can range from 0.01 to about 30 mg/ml preverably about 0.17 to about 1.5 mg/ml. Finally, technetium-99m in the form of pertechnetate can be in amounts used up to about 500 uCi/ml preferably about 1–50 mCi/ml. The amount of mCi per mg of antibody is preferably about 3–150.

The reaction between the and the metal ion-transfer ligand complex is preferably carried out in an aqueous solution at a pH at which the protein is stable. By "stable", it is meant that the protein remains soluble and retains its biological activity. Normally, the pH for the reaction will be a pH from about 5 to 9, the preferred pH being about 6–8. The metal ion-transfer chelate complex and the antibody are incubated, preferably at a temperature from about 20° C. to about 60° C., most preferably from about 20° C. to about 37° C., for a sufficient amount of time to allow transfer of the metal ion from the ligand complex to the antibody. Generally, less than one hour is sufficient to complete the transfer reaction under these conditions.

Kits For Performing The Method

The reagent for performing the labeling method can be assembled in kits for convenient performance of the method in the clinic. At minimum, a kit for radiolabeling antibody or antibody fragments with the radiometals can consist of a one component a via (sealed and sterile) containing a reducing agent (preferably stannous ions) and saccharic acid or a salt thereof. These kits can be used when the antibody or antibody fragment is provided by the user.

Kits may also include a second vial containing the sulfhydryl-containing antibody or antibody fragment to be labeled. Two component kits would include:
a. a vial containing a reducing agent and a water-soluble transfer ligand; and
b. a sulfhydryl-containing antibody or antibody fragment under non-oxiding conditions.

Kits can be designed to contain the appropriate antibody or antibody fragment(s) for any particular immunodiagnostic or immunotherapeutic procedure (some of which are discussed below).

The reagents in the kit can be provided in aqueous, lyophilized or from form. Lyophilized preparations can be diluted with aqueous medium upon use. The amount of reagents in each vial can vary according to the chosen parameters of the method (see above under Reaction Conditions).

When reagents are provided as a two component kit, as described, the labeling procedure can be performed simply as a two vial technique. Technetium-99m (for example, in the form of aqueous sodium pertechnetate) is added to the vial containing the reducing agent and the water-soluble ligand in aqueous solution. The contents of the two vials are then mixed and incubated for a time sufficient to effect labeling of the antibody or antibody fragment. The radiolabeled antibody or antibody fragment can then be used immediately without purification.

Use of the Labeled Antibodies in Immunodiagnostics

Technetium-99m labeled antibodies or antibody fragments can be used in immunoscintigraphy. One important use is in the imaging of tumors. As mentioned, antibody fragments are preferred for most immunoscintigraphic techniques. Labeled Fab' fragments of tumor specific antibodies can be prepared and used to image primary or secondary tumors. In general, the technetium-99m labeled antibody fragment is prepared by forming an aqueous mixture of (i) 99m Tc; and (ii) a reducing agent and a water-soluble ligand; and contacting the mixture with an Fab' fragment specific for the tumor.

The labeled Fab' fragment can then be injected parenterally (preferably intraveneously) into a subject. After injection, sufficient time is allowed for the labeled Fab' fragment to accumulate at the site of the tumor. The subject is then scanned with a gamma camera to detect the gamma emission of the technetium-99m and to thereby to obtain an image of the tumor. In this way the tumor can be localized and its size can be determined.

Tumor-specific antibody fragments for use in these procedures can be derived from anticolorectal cancer antibody, antilung cancer antibody antiovarian cancer antibody, antibreast cancer antibody, and antiprostate cancer antibody. Some specific examples of tumor specific antibodies which can be labeled by the method of this invention and used to image tumors are the monoclonal antibodies 17-1A and 19-9 (gastrointestinal), CA 125 (ovarian) and 103D2 (breast).

Antibodies labeled by the method of this invention can be used to label myocardial infarcts. The imaging of myocardial infarcts to determine their size and location is described by Haber, U.S. Pat. No. 4,421,735. In brief, employing the labelling method of this invention, an image of a mycocardial infarct in a subject can be obtained by first preparing a Tc-99m labeled myosin specific Fab' fragment by first forming an aqueous mixture of (i) $^{99m}Tc$ and (ii) a reducing agent and a water soluble ligand for $^{99m}Tc$; and then contacting the mixture with a myosin specific Fab' fragment. The labeled myosin specific fragment is then intraveneously injected into a subject (for example, after coronary occlusion). The labeled fragment is allowed to localize at the site of the infarct and an image of the infarct is obtained by scanning the area of the heart with a gamma camera.

A preferred antibody for production of labeled myosin-specific Fab' fragments is the monoclonal antibody R11D10.

In addition, fibrin-specific Fab' fragments can be labelled by the procedure of this invention to provide reagents for imaging blood clots. A Tc-99m labeled fibrin-specific fragment is prepared by forming an aqueous mixture of (i) $^{99m}Tc$ and (ii) a reducing agent and a water soluble ligand for $^{99m}Tc$ and contacting the mixture with a fibrin specific Fab' fragment. The $^{99m}Tc$-labeled fibrin specific fragment is injected into the subject. After allowing the fragment to localize at the site of the blood clot, the subject is scanned to obtain an image of the clot. Fibrin-specific antibodies which are not cross-reactive with fibrinogen are the preferred antibodies for this imaging technique.

Antibody fragments specific for bacteria can be used in immunoscintigraphic techniques for obtaining an image of a bacterial abscess in a subject. For this purpose, anti-bacterial or anti-macrophage antibody fragments are employed. Antibodies against a common determinant of gram-negative bacteria (e.g., anti-lipid A antibody) can be used to image an abscess caused by a gram-negative microorganism. The antibody is labeled with technetium-99m as described above injected into the subject and allowed to localize at the abscess. The subject is then scanned with the photoscanning equipment to obtain an image of the abscess.

Radioimmunotherapeutics

Rhenium-labeled antibody or antibody fragments can be used to selectively deliver rhenium radioisotopes to target cells in vivo. For example, rhenium labeled antibodies can selectively seek out and destroy cancer cells. For this purpose, tumor specific antibodies, such as those described above, can be labeled by the method of this invention and the resulting labeled antibody can be injected parenterally into a subjected afflicted with the tumor.

The invention is further illustration by the following exemplification.

Exemplification

EXAMPLE 1

Radiolabeling of Antimyosin Antibody R11D10 Fab' with Technetium-99m using $^{99m}Tc$-Saccharate Preparation of $^{99m}Tc$-Saccharate Monopotassium saccharate (25 mg) was dissolved in 0.2M bicarbonate (1.0 ml) at pH 8.0. To 500 $\mu$l of saccharate solution was added 40 $\mu$l of stannous chloride (2.5 mg/ml) in 0.1M acetic acid followed by 500 ul of Tc-99m generator eluate ($\geq$60 mCi/mg protein). The resulting solution was allowed to stand for 5 minutes at room temperature and then analyzed for radiochemical purity by paper chromatgraphy (Whatman 3MM, 60% $CH_3CN:40\%H_2O$).

Preparation of R11D10 Fab'

Antimyosin monoclonal antibody R11D10 F(ab')$_2$ 5 mg/ml in 40 mM TRIS pH 7.0 was reduced with 10 mM DTT for 60 minutes at room temperature and then passed through a Sephadex G-25 column to remove the reducing agent. The resulting solution contained $\geq$80% Fab' fragment by gel-filtration HPLC.

Labeling of R11D10 Fab' using $^{99m}Tc$-Saccharate

Antimyosin antibody R11D10 Fab' (500 $\mu$l of a 1 mg/ml solution) in 50 mM phosphate, 0.35 mM $ZnCl_2$, pH 6.5 was mixed with 500 ul of $^{99m}Tc$-saccharate solution and allowed to stand at room temperature for 5–60 minutes. The resulting $^{99m}Tc$-labeled protein was analyzed for radiochemical purity by paper chromatography (Whatman 3MM; 60% $CH_3CN$: 40%$H_2O$) and gel-filtration HPLC, and for immunoreactivity using a myosin affinity column.

EXAMPLE 2

The effect of Saccharate Concentration on the Formation of $^{99m}Tc$-Saccharate $^{99m}Tc$-Saccharate was prepared as described in Example 1 using different concentrations of potassium saccharate (0.09–12.25 mg/ml). The products were analyzed by paper chromatography (Whatman 3MM, 60% $CH_3CN/40\%$ $H_2O$; $^{99m}TcO_4^-$ Rf=1.0, $^{99m}Tc$-saccharate, Rf=0.4; $^{99m}TcO_2.x$ $H_2O$, Rf=0). The data in Table I show that a concentration of 6 mg/ml potassium saccharate in 0.2M bicarbonate is sufficient to completely stabilize the reduced technetium.

EXAMPLE 3

Stability of $^{99m}Tc$-Saccharate

Samples of $^{99m}Tc$-saccharate prepared from 6 and 12 mg/ml potassium saccharate were analyzed over a period of 7 hours. The results (Table II) indicated that the preparation from 12 mg/ml saccharate was more stable and was stable for a period of about 2 hours.

EXAMPLE 4

The effect of Antibody Concentration on the Labeling of R11D10 Fab' using $^{99m}$Tc-Saccharate $^{99m}$Tc-labeled R11D10 Fab' was prepared as described in Example 1 using various protein concentrations up to 1250 μg/ml. After 1 hour, the reaction mixtures were analyzed by paper chromatography and HPLC. The results (Table III) showed that the radiochemical yield was dependent upon the concentration of the protein and that quantitative labeling could be obtained in 1 hour using at least 340 μg/ml.

EXAMPLE 5

Evaluation of the Transfer of Technetium from $^{99m}$Tc-Saccharate to Non-Reduced Antibody/Fragments compared to Fab' Fragments 100 ul of whole antibody (2 mg/ml), F(ab')$_2$ (2 mg/ml), Fab' (1 mg/ml) of antimyosin antibody R11D10, antipancreatic antibody 19-9 and anticolorectal antibody 17-1A were incubated with 100 ul $^{99m}$Tc-saccharate solution at room temperatures for 1 and 3 hours. The resulting products were analyzed by paper chromatography. The results (Table IV) showed that the labeling of non-reduced antibody/fragments was less than 5% versus quantitative labeling of the Fab' fragments.

EXAMPLE 6

Labeling of R11D10 Fab' Using $^{99m}$TC-glucoheptonate to Non-Reduced Antibody/Fragments Compared to Fab' Fragments R11D10 Fab' (1 mg/ml) was incubated with $^{99m}$Tc-glucoheptonate at room temperature for one hour. Analysis by paper chromatography indicated quantitative transfer of the technetium to the antibody.

EXAMPLE 7

Technetium-99m Labeling of Anti-Colorectal Antibody 17-1A Fab' and Antimyosin Antibody R11D10 Fab'

Both antibody fragments were prepared and labeled as described in Example 1. Gel filtration HPLC analysis of the products after three hours at room temperature shows that for the 17-1A 35% of the protein was in the form of F(ab')$_2$ and 65% Fab' whereas for R11D10 23% was in the form of F(ab')$_2$ and 77% as Fab'. However, radioactive detection showed that 80% of the radioactivity was associated with the Fab' peak for both antibodies. These results shows that the $^{99m}$Tc-saccharate preferentially labels the Fab' fragments.

EXAMPLE 8

Radiochemical Stability of $^{99m}$Tc-Labeled Fab' Antibody Fragments $^{99m}$Tc-labeled 17-1A Fab' and R11D10 Fab' were incubated at 37° C. for 1 hour in the presence and absence of human plasma. The results (Table V) showed that 80% of the technetium remained bound to the antibody for over 20 hours even in the presence of plasma.

EXAMPLE 9

Immunoreactivity of $^{99m}$Tc-labeled R11D10 Fab'

Immunoreactivity of $^{99m}$Tc-R11D10 Fab' preparation was determined using a myosin affinity column. $^{99m}$Tc-17-1A was used as a control to estimate non-specific binding. Each labeled protein was incubated at 37° C. in the presence of human plasma.

As shown in Table VI, the $^{99m}$Tc-labeled R11D10 Fab' was nearly 80% immunoreactive after 3 hours and 70% immunoreactive after 20 hours. The latter corresponded to 80% retention of immunoreactivity found immediately after labeling.

EXAMPLE 10

Detection of Myocardial Infarct In The Dog Using $^{99m}$Tc-R11D10 Fab'

Mongrel dogs (n=6) were anesthetized with I.V. pentobarbitol (30 mg/kg), and respiration maintained on a Harvard respirator. Left thoracotomy was performed, the heart suspended in a pericardial cradle and a segment of the left anterior descending coronary artery approximately two thirds the distance from the apex to the base was dissected free. The LAD was then occluded with a silk ligature.

Figure 2:
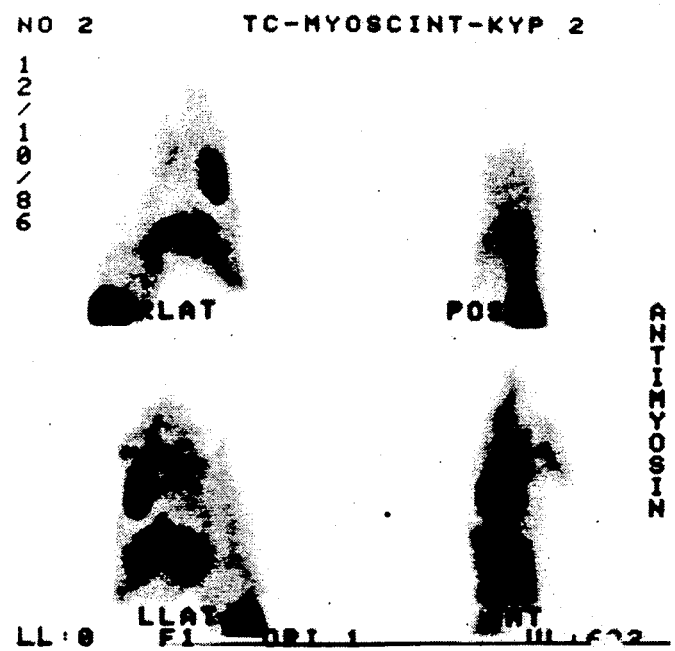
FIG. 2 shows gamma scintigrams of the same dog taken from different views.

After three hours of LAD occlusion, the occlusive ligature was removed and reperfusion was established. At 15 minutes of reperfusion, 200 uCi of indium-111 labeled R11D10 Fab-DTPA was injected and 30 seconds later, 10 mCi of technetium labeled R11D10 Fab' was injected. Serial imaging with a gamma camera was initiated immediately upon tracer administration. FIG. 1 shows the gamma scintigrams of a dog after 35 min. (upper left), 1.5 hours (upper right), 2.5 hours (lower left) and 5 hours (lower right) of antibody injection. FIG. 2 shows the gamma images of the same dog as shown in FIG. 1, right lateral (upper left), posterior anterior (lower right) views. Clear myocardial infarct images were observed in all views except the posterior position. More importantly, this figure shows no significant liver uptake 3 hours after injection of Tc-R11D10-Fab'.

EXAMPLE 11

Biodistribution Studies of Technetium-99m Labeled R11D10 Fab' and of the Indium-111 Labeled R11D10 Fab-DTPA in Mice Biodistribution studies were carried out in Balb/c mice. The mice (4 mice per group) were injected I.V. with either 150 μCi of technetium-99m labeled R11D10 Fab' (4 μCi/ug) or 10 μCi of indium-111 labeled R11D10 Fab-DTPA (4 μCi/ug).

Groups of mice were sacrificed at 1,4 and 8 hours after receiving the injections and organs removed, weighed and counted. Table VII summarizes the percent injected dose per gram obtained for each preparation.

The $^{99m}$Tc-R11D10 Fab' cleared rapidly from both the blood and liver. The percent of injected dose for Tc-R11D10 Fab' in the blood at 1 hour was 13.6% and dropped to 2.0% after eight hours. A similar drop in radioactivity was observed in the liver at the latter time point (6.4% in 1 hour and 2.4% in eight hours). However, the indium-111 labeled preparation showed much higher radioactivity in both liver (10.8%) and blood (5.1%) at the eighth hour after injection.

EXAMPLE 12

R11D10 Fab' With Technetium-99m Using $^{99m}$Tc-Arabonate

Preparation of $^{99m}$Tc-Arabonate

Monopotassium arabonate (20 mg) was dissolved in 0.1M Na (1.0 ml) at pH 10.0. To 500 μl of arabonate solution was added 500 μl of Tc-99m generator eluate (approx. 60 mCi/mg protein) followed by 40 μl of stannous chloride (2.5 mg/ml) in 0.1M acetic acid. The resulting solution was allowed to stand at room temperature for 30 minutes and then adjusted to pH 7 using 1.0M hydrochloric acid.

The sample was analyzed for radiochemical purity by paper chromatography (Whatman 3MM, 60% $CH_3CN$:40% $H_2O$).

Preparation of R11D10 Fab'

The same procedure as outlined in Example 1 was employed for preparation of R11D10 Fab'.

Preparation of R11D10 Fab' Using $^{99m}$Tc-Arabonate

Antimyosin antibody R11D10 Fab' (500 ul of a 1 mg/ml solution) in 50 mM phosphate, 0.35 mM $ZnCl_2$, pH 6.5 was mixed with 500 ul of $^{99m}$Tc-arabonate solution and allowed to stand at room temperature for 60 minutes. The resulting $^{99m}$Tc-labeled protein was analyzed for radiochemical purity as previously noted in Example 1. The results showed quantitative transfer of $^{99m}$Tc to the protein under these conditions.

EXAMPLE 13

Radiolabeling of Antimyosin R11D10 Fab' with Technetium $^{99m}$ Using $^{99m}$Tc-Tartarate Preparation of $^{99m}$Tc-Tartarate Disodium tartarate (230 Mg) was dissolved in 0.1M $Na_2CO_3$ (1.0 ml) at pH 10.0. To 500 ul of tartarate solution was added 500 ul of Tc-99m generator eluate (approx. mCi/mg protein) followed by 40 ul of stannous chloride (2.5 mg/ml) in 0.1M acetic acid. The resulting solution was allowed to stand at room temperature for 30 minutes and then adjusted to pH 7 using 1.0M hydrochloric acid. The sample was analyzed for radiochemical purity as previously outlined in example 1 (see Page 13).

Preparation of R11D10 Fab'

The same procedure as outlined earlier in Example 1 was used to prepared R11D10 Fab'.

Preparation of R11D10 Fab' Using $^{99m}$Tc-Tartarate

Antimyosin antibody R11D10 Fab' (500 μl of a 1 mg/ml solution) in 50 mM phosphate, 0.35 mM $ZnCl_2$, pH 6.5 was mixed with 500 ul of $^{99m}$Tc-tartarate solution and allowed to stand at room temperature for 60 minutes. The Tc-99m protein labeled product was analyzed as previously outlined in Example 1.

The results showed quantitative transfer of $^{99m}$Tc to the protein under these conditions.

TABLES

TABLE 1

Percent of $^{99m}TcO_2$ and $^{99m}$Tc-Saccharate After Incubation at Room Temperature for 1 Hr. at Various Concentrations of Saccharic Acid as Analyzed by Paper Chromatography.

| Saccharic Acid (mg/ml) | % $^{99m}TcO_2$ | % $^{99m}$Tc-Saccharate |
|---|---|---|
| 12.25 | .0 | 100.0 |
| 6.12 | .0 | 100.0 |
| 3.06 | 11.5 | 88.5 |
| 1.53 | 19.5 | 80.5 |
| 0.76 | 24.4 | 75.6 |
| 0.38 | 30.0 | 70.0 |
| 0.19 | 41.0 | 59.0 |
| 0.09 | 57.0 | 43.0 |

TABLE II

Stability of $^{99m}$Tc-Saccharate at room temperature

| Time Hours | 6.12 mg/ml | | 12.24 mg/ml | |
|---|---|---|---|---|
| | % Tc-SACC | % $TcO_4^-$ | % Tc-SACC | % $TcO_4^-$ |
| 1 | 95 | 5 | 95 | 5 |
| 3 | 76 | 24 | 82 | 18 |
| 5 | 45 | 55 | 62 | 38 |
| 7 | 36 | 64 | 60 | 40 |

TABLE III

Percent of $^{99m}$Tc-Labeled R11D10 Fab' After Labeling with $^{99m}$Tc-Saccharate at Different Protein Concentration as Analyzed by Paper and HPLC Gel Filtration Chromatography.

| Protein Concentration (μg/ml) | % $^{99m}$Tc-Labeled Ab | % $^{99m}$Tc-Saccharate |
|---|---|---|
| 1250 | 100.0 | 0 |
| 340 | 100.0 | 0 |
| 165 | 72.0 | 28.0 |
| 133 | 66.2 | 33.8 |
| 100 | 67.0 | 33.0 |
| 33 | 53.0 | 47.0 |
| 0 | 0.0 | 100.0 |

TABLE IV

Evaluation of the transfer of $^{99m}$technetium as $^{99m}$Tc-Saccharate to reduced vs. non-reduced antibody/fragments.

| Ab | % Labeling at (1 HR) | % Labeling at (3 HR) |
|---|---|---|
| R11D10 IgG | 3.6 | 3.6 |
| R11D10 F(ab')$_2$ | 1.6 | 1.0 |
| R11D10 Fab-DTPA | 4.4 | 3.2 |
| R11D10 Fab' | 100.0 | 100.0 |
| 19-9 IgG | 4.0 | 4.1 |
| 19-9 F(ab)$_2$ | 4.3 | 2.4 |
| 19-9 Fab' | 100.0 | 100.0 |
| 17-1A IgG | 2.7 | 1.5 |
| 17-1A F(ab')$_2$ | 3.0 | 1.4 |
| 17-1A Fab' | 100.0 | 100.0 |

TABLE V

Stability of $^{99m}$Tc-labeled 17-1A Fab' and $^{99m}$Tc-labeled R11D10 Fab' in the Absence and Presence of Human Plasma

| | % Tc-labeled Ab | | | |
|---|---|---|---|---|
| | 3 hours | | 20 hours | |
| | Absence H. Plasma | Presence H. Plasma | Absence H. Plasma | Presence H. Plasma |
| 17-1A Fab' | 82 | 85 | 93 | 84 |
| R11D10 Fab' | 82 | 83 | 86 | 86 |

TABLE VI

Immunoreactivity of Tc-labeled R11D10 Fab'

| | % of Binding | | |
|---|---|---|---|
| | 0 hours | 3 hours | 20 hours |
| Tc-17-1A Fab' | 1.2 | 2.2 | 3.3 |
| R11D10 Fab' | 81 | 79 | 70 |

TABLE VII

Biodistribution in % injected dose per gram of Indium labeled R11D10 Fab-DTPA and Technetium-99m labeled R11D10 Fab' at 1, 4, and 8 hours post injection in mice.

| Tissue | One Hour | Four Hours 99mTc-In-111- | | Eight Hours 99mTc-In-111 |
|---|---|---|---|---|
| | | | 99mTc-In-111- | |
| Blood | 13.62 ± 04.52 | 06.92 ± 00.64 | 04.82 ± 01.00 | 05.11 ± 00.49 | 02.02 ± 00.48 |
| Spleen | 03.36 ± 01.51 | 03.26 ± 01.53 | 04.51 ± 03.04 | 04.97 ± 01.11 | 02.31 ± 01.17 |
| Stomach | 02.34 ± 00.83 | 02.07 ± 00.25 | 00.89 ± 00.35 | 01.51 ± 01.04 | 00.31 ± 00.23 |
| Intestine | 02.74 ± 01.00 | 02.72 ± 00.18 | 01.49 ± 00.04 | 02.53 ± 00.07 | 00.75 ± 00.24 |
| Kidney | 115.00 ± 32.30 | 36.88 ± 09.38 | 81.10 ± 15.40 | 58.90 ± 05.10 | 57.67 ± 22.61 |
| Liver | 06.44 ± 01.87 | 08.82 ± 00.91 | 03.68 ± 00.52 | 10.79 ± 00.36 | 02.36 ± 00.95 |
| Lung | 07.89 ± 03.32 | 05.62 ± 01.60 | 03.60 ± 00.93 | 03.74 ± 00.87 | 01.61 ± 00.57 |
| Heart | 08.77 ± 04.16 | 03.00 ± 00.28 | 03.00 ± 01.13 | 03.10 ± 00.80 | 01.33 ± 00.05 |
| Muscle | 01.31 ± 00.17 | 01.53 ± 00.16 | 00.83 ± 00.32 | 01.82 ± 00.5 | 00.42 ± 00.11 |
| Bone | 00.63 ± 00.24 | — | 00.90 ± 00.17 | — | 00.92 ± 00.38 |

— Not available

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of labeling a sulfhydryl-containing antibody or binding fragment thereof with a radiometal selected from the group consisting of technetium-99m, rhenium-186, rhenium-188, rhenium-189 and rhenium-191, comprising the steps of:
   a. forming a mixture of:
      i) the radiometal; and
      ii) a reducing agent and a water-soluble polyhydroxycarboxylic acid ligand, the ligand being capable of complexing the radiometal to form a soluble radiometal-ligand complex;
   b. contacting the mixture with a sulfhydryl-containing antibody or antibody fragment under conditions which permit transfer of the radiometal to the antibody or fragment to form a radiometal-labeled antibody or antibody fragment.

2. A method of claim 1, wherein the sulfhydryl containing antibody is a reduced IgG.

3. A method of claim 1, wherein the antibody fragment is a Fab' fragment.

4. A method of claim 1 wherein Fab' is produced by reducing an F(ab')$_2$ with DTT.

5. A method of claim 1, wherein the water soluble polyhydroxycarboxylic acid ligand is a compound or salt thereof represented by the formula:

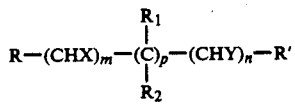

where X and Y are OH or NH$_2$;

R and R' are independently H, COOH, or CH$_2$OH, or R and R' taken together can form a ring or bi-or multidentate ligand;

m and n are 0–10 such that m+n is at least 2;

R$_1$ and R$_2$ are independently H, lower alkyl, substituted lower alkyl, aryl or lower alkylaryl; and p is 1 and m and n independently are at least 1.

6. A method of claim 5 wherein the ligand is a compound or salt thereof represented by the formula:

R—(CHOH)$_n$—R' wherein R and R' are COOH or CH$_2$OH and n = 2 – 10.

7. A method of claim 6, wherein the ligand is a polyhydroxydicarboxylic acid or salts thereof, of molecular weight less than about 10,000 daltons.

8. A method of claim 7, wherein the ligand is selected from the group consisting of saccharic acid, glucoheptonic acid, tartaric acid, galactaric acid, arabonic acid and salts thereof.

9. A method of claim 8, wherein the water soluble ligand is saccharic acid or a salt thereof.

10. A method of claim 1, wherein the reducing agent is a stannous reducing agent.

11. A method of labeling a Fab' fragment with Technetium-99m, comprising the steps of:
   a. forming a mixture of:
      i) Tc-99m in an oxidized state; and
      ii) a composition comprising a reducing agent and a polyhydroxycarboxylic acid ligand of the formula:

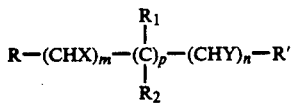

where X and Y are OH or NH$_2$;

R and R' are independently H, COOH, or CH$_2$OH, or R and R' taken together can form a ring or bi-or multidentate ligand;

m and n are 0–10 such that m+n is at least 2;

R$_1$ and R$_2$ are independent H, lower alkyl, substituted lower alkyl, aryl or lower alkylaryl; and p is 1, and m and n independently are at least 1; and b. contacting the mixture with an Fab' fragment to produce a Tc-99m labeled Fab' fragment.

12. A method of claim 11, wherein the Fab' fragment is produced by reducing an F(ab')$_2$ fragment.

13. A method of claim 11, wherein the reducing agent is a stannous reducing agent.

14. A method of claim 13, wherein the stannous reducing agent is stannous chloride.

15. A method of claim 11, wherein the Technetium-99m is used as a pertechnetate.

16. A method of claim 11, wherein the ligand is represented by the formula:

$$R-(CHOH)_n-R'$$

wherein R and R' are COOH or $CH_2OH$, and $n = 2-10$.

17. A method of claim 16 wherein the ligand is a polyhydroxydicarboxylic acid or salt thereof having a molecular weight of less than about 10,000 daltons.

18. A method of claim 17 wherein the ligand is selected from the group consisting of saccharic acid, glucoheptonic acid, tartaric acid, muccic acid, arabonic acid and salts thereof.

19. A method of claim 18 wherein the ligand is saccharic acid or a salt thereof.

20. A method of claim 11, wherein the Fab' fragment is derived from an anti-myosin, anti-fibrin, or anti-platelet antibody.

21. A method of claim 11, wherein the Fab' fragment is derived from an anti-tumor antibody.

22. A method of claim 21, wherein the anti-tumor antibody is an anti-colorectal cancer antibody, anti-ovarian cancer antibody, anti-lung cancer antibody, anti-breast cancer antibody or anti-prostate cancer antibody.

23. A method of claim 11, wherein the Fab' fragment is derived from an antibacterial or anti-macrophage antibody.

24. A method of labeling a Fab' fragment with technetium-99m, comprising the steps of:
   a. reacting aqueous pertechnetate-99m with a water-soluble polyhydroxycarboxylic acid ligand in the presence of a reducing agent to form a stabilized complex of the ligand and Technetium-99m in a reduced state; and
   b. thereafter, reacting a Fab' fragment with the complex to form a Tc-99m-labeled Fab' fragment.

25. A method of claim 24, wherein the reducing agent is stannous ions and the ligand is saccharic acid or a salt thereof.

26. A method of labeling a sulfhydryl containing antibody or antibody fragment with technetium-99m, comprising the steps of:
   a. forming an aqueous mixture of pertechnetate-99m, a stannous reducing agent and saccharic acid; and
   b. combining the mixture and sulfhydryl containing antibody or antibody fragment to produce a Technetium-99m labeled antibody or antibody fragment.

27. A method of claim 26, wherein the antibody fragment is a Fab' fragment.

28. A method for labeling a Fab' fragment with technetium-99m, comprising:
   a. adding sodium pertechnetate-99m to a first vial containing an aqueous solution of stannous reducing agent and saccharic acid or a salt thereof; and
   b. thereafter mixing the contents of the first vial with the contents of a second vial containing an aqueous solution of an Fab' fragment under non-oxidizing conditions.

* * * * *